(12) United States Patent
Fahey et al.

(10) Patent No.: US 7,303,770 B2
(45) Date of Patent: *Dec. 4, 2007

(54) CANCER CHEMOPROTECTIVE FOOD PRODUCTS

(75) Inventors: Jed W. Fahey, Eldersburg, MD (US); Paul Talalay, Baltimore, MD (US)

(73) Assignee: Johns Hopkins School of Medicine, Baltimore, MD (US)

( * ) Notice: Subject to any disclaimer, the term of this patent is extended or adjusted under 35 U.S.C. 154(b) by 1141 days.

This patent is subject to a terminal disclaimer.

(21) Appl. No.: 09/825,989

(22) Filed: Apr. 5, 2001

(65) Prior Publication Data

US 2001/0031287 A1   Oct. 18, 2001

Related U.S. Application Data

(62) Division of application No. 09/425,890, filed on Oct. 25, 1999, now Pat. No. 6,242,018, which is a division of application No. 09/118,867, filed on Jul. 20, 1998, now Pat. No. 6,177,122, which is a division of application No. 08/840,234, filed on Apr. 11, 1997, now Pat. No. 5,968,567.

(51) Int. Cl.
  *A01N 65/00* (2006.01)
  *A61K 36/00* (2006.01)
  *A23L 1/28* (2006.01)
  *B09B 3/00* (2006.01)

(52) U.S. Cl. ............ 424/725; 424/755; 424/774; 424/776; 424/779; 426/425; 426/429; 426/431; 426/489; 426/615; 426/629; 426/655; 210/755; 210/766; 210/767; 210/768; 210/774; 210/904

(58) Field of Classification Search ............ 426/425, 426/429, 431, 615
  See application file for complete search history.

(56) References Cited

U.S. PATENT DOCUMENTS

| | | | |
|---|---|---|---|
| 3,108,040 A | | 10/1963 | Folkers |
| 4,083,836 A | * | 4/1978 | Anjou et al. ............ 260/123.5 |
| 4,158,656 A | * | 6/1979 | Jones et al. ............ 260/123.5 |
| 4,191,752 A | | 3/1980 | Kada et al. |
| 5,290,578 A | * | 3/1994 | Passey et al. ............ 426/417 |
| 5,411,986 A | | 5/1995 | Cho et al. ............ 514/514 |
| 5,686,108 A | * | 11/1997 | Pusateri et al. ............ 424/464 |
| 5,725,895 A | | 3/1998 | Fahey et al. ............ 426/49 |
| 5,882,646 A | * | 3/1999 | Pusateri et al. ............ 424/195.1 |
| 6,436,450 B1 | * | 8/2002 | Omary et al. ............ 424/755 |
| 6,991,811 B1 | * | 1/2006 | Brovelli et al. ............ 424/725 |

FOREIGN PATENT DOCUMENTS

WO    WO 94/19948 A1    9/1994
WO       9707230     *   2/1997

OTHER PUBLICATIONS

McDanell et al., "The Effect of Feeding *Brassica* Vegetables and Intact Glucosinolates on Mixed-Function-Oxidase Activity in the Livers and Intestines of Rats," *Fed. Chem. Toxic.*, vol. 27, No. 5, pp. 289-293 (1989) © Maxwell Pergamon Macmillan plc.
Graham et al., "Diet in the Epidemiology of Cancer of the Colon and Rectum," J. Natl. Cancer Inst., vol. 61, No. 3, Sep. 1978.
The Sproutletter, No. 25, Nov.-Dec. 1984.
"The Sproutletter" May-Jun. 1981, No. 4.
Roy Bruder, Ph.D., Discovering Natural Foods, (including pp. 203-209), Woodbridge Press, 1982.
Brian R. Clement, Hippocrates Health Program, (including pp. 7-11), Hipprocrates Publications, 1989.
Jethro Kloss, The Back to Eden Cookbook, pp. 61-61, Woodbridge Press, 1974.
Steve Meyerowitz, Sproutmann Kitchen Garden Cookbook, the Sprouthouse, Inc., pp. 178-179, 290, 1994.
Steve Meyerowitz, Sprout It, One week from Seed to Salad, The Sprouthouse, Inc., (including pp. 84-85, 120-123), Jun. 1994.
Steve Meyerowitz, the Complete Guide to Sprouting, Sprouts The Miracle Food, Sproutman Publications, (including pp. 121-122), May 1998.
Esther Munroe, Sprouts to Grow and Eat, (including pp. 2-15), Dec. 1974.
Jean Hewitt, The New York Times New Natural Foods Cookbook:, Avon Books, pp. 200-203, 1982.
Martha H. Oliver, Add a Few Sprouts To Eat Better for Less Money, Pivot Original Health Books, (including pp. 52-53, 118-119), 1975.
James C. Schmidt, Horticulture Facts, "Growing Sprouts Indoors", (Rev. 4/81), 1981.
Angnes Toms, The Joy of Eating Natural Foods, The Complete Organic Cookbook, pp. 318-319, Nov. 1971.
Karen Cross Whyte, The Complete Sprouting Cookbook, Troubador Press, (including pp. 57-59), 1973.
Ann Wigmore, The Sprouting Book, Avery Publications, (including pp. 29-37), 1986.
Debra Schwarze, Growing Sprouts, Neb Guide, Jan. 1989.
John Tobe, Sprouts Elixir of Life, 1970.
Alicia Bay Laurel, "Living on the Earth" a Vintage Book, 1980.
David Ehrlich with George Wolf, Foreward by Peter Albright, M.D., "The Bowell Book", Schocken Books, 1981.
"The Good News Sprouts Recipe Book" ISGA, Aug. 1992.
Ann Wigmore, "The Hippocrates Diet and Health Program", Avery Publications, 1984.
Sprouting Publications Oahspe Foundation, health and Sprouting Supplies, 1982.
Sproutletter, #41, Summer, 1989.
The Sproutletter, No. 27, Mar.-Apr. 1985.
Steve Meyerowitz, Growing Vegetables Indoors, 1983.
The Sproutletter, No. 24, Sep.-Oct. 1984.
The Sproutletter, Issue 33, Spring 1987.
The Sproutletter, No. 28, May-Jun. 1985.
The Spouterletter, No. 26, Jan.-Feb. 1985.
Sprouting Publications, Health and Sprouting Supplies, 1982.

(Continued)

*Primary Examiner*—Frederick Krass
(74) *Attorney, Agent, or Firm*—Foley & Lardner LLP

(57) ABSTRACT

Vegetable sources of cancer chemoprotective agents have been identified which are extraordinarily rich in glucosinolates, metabolic precursors of isothiocyanates. The vegetable sources are used to provide a dietary means of reducing the level of carcinogens in mammals.

26 Claims, 2 Drawing Sheets

OTHER PUBLICATIONS

The Sproutletter, No. 29, Jul.-Aug. 1985.
Sproutletter, #40, Spring, 1989.
The Sproutletter, No. 32, Summer, 1985.
Sprouterletter, #44, Mar. 1991.
Sproutletter, #36, Winter, 1987-88.
Sproutletter, #39, Fall, 1988.
Sproutletter, #43, May/Jun. 1990.
Sproutletter, #38, Summer, 1988.
Sprouting Publications Health and Sprouting Supplies, 1988.
Spring Sale for Members Only, 1988.
The Sproutletter, A newletter of useful and unusual information on sprouts, raw foods and nutrition, 1987.
The Sproutletter, #31, Winter, 1989.
Deirdre Purdy, ed., The Summer Kitchen, A Farmers' Market Cookbook, 1981.
Viktoras Kulvinskas, M.S. Co-Director Hippocrates Health Institute, "Love Your Body or how to be a live food lover", 1974.
The Sprout House Article from Newspaper, 1988.
New Prices—New Products, Jul. 1985 order form.
Steve Meyerowitz, Indoor Vegetable Kit, The Sprout House, 1985.
The Sprout House Newsletter, Issue #15, Aug. 1992.
Sproutman's Exotic Seeds for Sprouting 100% Organically Grown Order Form, 1985.
Complaint for Patent Infringement (*Brassica* Protection Products, LLC v. The Sproutman, Inc. dated Sep. 20, 1999.
Murry Tizer's Answer, Affirmative Defenses and Counterclaims dated Jun. 28, 1999.
The Sproutman, Inc.'s Answer, Affirmative Defenses and Counterclaims dated Jun. 28, 1999.
Request for Reexamination of U.S. Patent No. 5,725,895 filed Oct. 11, 1999.
Sprout it! One Week From Seed to Salad, Steve Meyerowitz (The Sprout House, Inc., Great Barrington, MA),. pp. 20-21, 58, 85-86, 120-123, 1993.
Munroe, E., Sprouts to Grow and Eat, the Steven Greene Press, (1974), pp. 2-9 and 14-15.
Schmidt, James C., Growing Sprouts Indoors, Cooperative Extension Service of the University of Illinois at Urbana-Champagne, College of Agriculture (1984) (pamphlet).
Whyta, K.C., The Complete Sprouting Cookbook, Troubader Press (1983), pp. 10-16, 57-60.
Posner et al., "Design and Synthesis . . . and potency as Inducers of Anticarcinogenic Detoxication Enzymes", Journal of Medicinal Chemistry, vol. 37, No. 1, pp. 170-175, 1994.
Zhang et al., "A major inducer of Anticarcinogenic protective enzymes from broccoli; isolation And education of structure", Proc. Natl. Acad. Sci. USA, vol. 89, pp. 2399-2403, Mar. 1992.
Prochaska et al. "Rapid detective od inducers of enzymes that protect against carcinogens", Proc. Nat'l. Sci. USA vol. 89, pp. 2394-2388, Mar. 1992.
Zhang et al., "Anticarcinogenic activities of sulforaphane and structurally related synthetic norbomyl isothiocyanates", Proc. Natl. Sci. USA, vol. 91, pp. 3147-3150, Apr. 1994.
Prochaska et al., Regulatory Mechanisms of Monofunctional and Bifunctional Anticarcinogenic Enzyme, Inducers in Murine Liver,: Cancer Research vol. 48, pp. 4776-4782, Sep. 1988.
Prochaska et al., "Direct Measurement of NAD(P)H: Quinone Reductase from Cells Cultured in Microtiter Wells: A Screening Assay for . . . Inducers", analytical Biochemistry, vol. 169, pp. 328-336, 1988.
Beecher, "Cancer prevention properties of varieties of *Brassica oleracea*: a review [1-3]", Am. J. Clin. Nutr.: 59 (suppl.) pp. 1166 s-1170s, 1994.
Presters et al., "Chemical and molecular regulation of enzymes that detoxity carcinogens", Proc. Natl. Acad. Sci. USA, vol. 90, pp. 2965-2969, Apr. 1993.
Zhand et al., "Anticarcinogenic Activities of Organic Isothiocyanates: chemistry and Mechanisms", Cancer Research suppl., 54, pp. 1976s-1981s, Apr. 1, 1994.
Tatalay, "The role of Enzyme Induction in Protection Against Carcinogenesis", Cancer Chemoprevention, pp. 469-478, 1992.
Prestera et al., "The Electrophile Counterattack Response: Protection Against Neoplasia and Toxicity", Advan. Enzyme Regul., vol. 33, pp. 281-296, 1993.
Masilungan et al., Screening of Philippine Medicinal Plants for Anticancer Agents using CCNSC "Protocols", Cancer Chemotherapy Reports (Part 2) vol. 2, No. 1, pp. 135-140, Apr. 1971.
Polasa et al., "Cancer preventive properties of varieties of *Brassica oleracea*: A review Source", American Journal of Clinical Nutrition 59 (5 Suppl), 1994.
Patent Abstract of Japan Sect. No. 305, vol. 9, No. 2371, p. 2, Sep. 1985.
Barrett et al., "Protective Effect of Cruciferous Seed Meals Against Mouse Colon Cancer", Cereal Foods World 613, vol. 39, No. 8, pp. 613, Aug. 1994.

\* cited by examiner

CANCER CHEMOPROTECTIVE FOOD PRODUCTS

This application is a divisional of U.S. Ser. No. 09/425,890, filed Oct. 25, 1999 and now U.S. Pat. No. 6,242,018, which is a divisional of U.S. Ser. No. 09/118,867, files Jul. 20, 1998 and now U.S. Pat. No. 6,177,122, which is a divisional of U.S. Ser. No. 08/840,234, filed Apr. 11, 1997 and now U.S. Pat. No. 5,968,567.

The U.S. Government has a paid-up license in this invention and the right in limited circumstances to require the patent owner to license others on reasonable terms as provided for by the terms of grant PO1 CA 44530, entitled "Novel Strategies for Chemoprotection Against Cancer", (Paul Talalay, Principal Investigator) awarded by the National Cancer Institute, Department of Health and Human Services.

BACKGROUND OF THE INVENTION

I. Field of Invention

This invention relates to a dietary approach to reducing the level of carcinogens in animals and their cells and thereby reducing the risk of developing cancer. In particular, this invention relates to the production and consumption of foods which are rich in cancer chemoprotective compounds. More specifically, this invention relates to chemoprotective compounds that modulate mammalian enzymes which are involved in metabolism of carcinogens. This invention relates to food sources which are extremely rich in compounds that induce the activity of Phase 2 enzymes, without inducing biologically significant activities of those Phase 1 enzymes that activate carcinogens.

II. Background

It is widely recognized that diet plays a large role in controlling the risk of developing cancers and that increased consumption of fruits and vegetables reduces cancer incidence in humans. It is believed that a major mechanism of protection depends on the presence of chemical components in plants that, when delivered to mammalian cells, elevate levels of Phase 2 enzymes that detoxify carcinogens.

Early studies on the mechanism of chemoprotection by certain chemicals assumed that these chemoprotectors induced activities of monooxygenases, also known as Phase 1 enzymes or cytochromes P-450. However, Talalay et al., [reviewed in "Chemical Protection Against Cancer by Induction of Electrophile Detoxication (Phase II) Enzymes" In: CELLULAR AND MOLECULAR TARGETS OF CHEMOPREVENTION, L. Wattenberg et al., CRC Press, Boca Raton, Fla., pp 469-478 (1992)] determined that administration of the known chemoprotector butylated hydoxyanisole (BHA) to rodents resulted in little change in cytochromes P-450 (Phase 1 enzyme) activities, but profoundly elevated Phase 2 enzymes. Phase 2 enzymes such as glutathione transferases, NAD(P)H:quinone reductase (QR) and glucuronosyltransferases, detoxify DNA-damaging electrophilic forms of ultimate carcinogens. Selective inducers of Phase 2 enzymes are designated monofunctional inducers. Prochaska & Talalay, *Cancer Res.* 48: 4776-4782 (1988). The monofunctional inducers are nearly all electrophiles and belong to 8 distinct chemical classes including (1) diphenols, phenylenediamines and quinones; (2) Michael reaction acceptors containing olefins or acetylenes conjugated to electron-withdrawing groups; (3) isothiocyanates; (4) 1,2-dithiole-3-thiones; (5) hydroperoxides; (6) trivalent inorganic and organic arsenic derivatives; (7) heavy metals with potencies related to their affinities for thiol groups including $Hg^{2+}$, and $Cd^{2+}$; and (8) vicinal dimercaptans. Prestera et al., *Proc. Natl. Acad. Sci. USA* 90: 2963-2969 (1993). The only apparent common property shared by all of these inducers is their ability to react with thiol groups.

Chemoprotective agents can be used to reduce the susceptibility of mammals to the toxic and neoplastic effects of carcinogens. These chemoprotectors can be of plant origin or synthetic compounds. Synthetic analogs of naturally occurring inducers have also been generated and shown to block chemical carcinogenesis in animals. Posner et al., *J. Med. Chem.* 37: 170-176 (1994); Zhang et al., *Proc. Natl. Acad. Sci. USA* 91: 3147-3150 (1994); Zhang et al., *Cancer Res.* (Suppl) 54: 1976s-1981s (1994).

Highly efficient methods have been developed for measuring the potency of plant extracts to increase or induce the activities of Phase 2 enzymes. Prochaska & Santamaria, *Anal. Biochem.* 169: 328-336 (1988) and Prochaska et al., *Proc. Natl. Acad. Sci. USA* 89: 2394-2398 (1992). In addition, these methods have been employed for isolating the compounds responsible for the inducer activities in plants and for evaluating the anticarcinogenic activities of these compounds and their synthetic analogs. Zhang et al., *Proc. Natl. Acad. Sci. USA* 89: 2399-2403 (1992) and Posner et al., *J. Med. Chem.* 17: 170-176 (1994).

Although inducer activity has been found in many different families of edible plants, the amounts are highly variable, depending on family, genus, species, variety, or cultivar of the plant selection and on growth and harvesting conditions. Thus, there is a need in the art to identify particular edible plants and methods of growing and preparing them that yield high levels of Phase 2 enzyme-inducer activity for chemoprotection. There is also a need for methods of growing and preparing edible plants that produce a known spectrum of specific inducers of Phase 2 enzyme activity in order to increase the efficiency with which specific carcinogens, or classes of carcinogens, are targeted for inactivation. In addition, there is a need for methods of plant breeding and selection to increase the level of Phase 2 inducer activity and to manipulate the spectrum of inducers produced in particular cultivars.

SUMMARY OF THE INVENTION

It is an object of the present invention to provide food products and food additives that are rich in cancer chemoprotective compounds.

Another object of the present invention is to provide food products which contain substantial quantities of Phase 2 enzyme-inducers and are essentially free of Phase 1 enzyme-inducers.

It is a further object of the present invention to provide food products which contain substantial quantities of Phase 2 enzyme-inducing potential and non-toxic levels of indole glucosinolates and their breakdown products and goitrogenic hydroxybutenyl glucosinolates.

These objects, and others, are achieved by providing cruciferous sprouts, with the exception of cabbage, cress, mustard and radish sprouts, harvested prior to the 2-leaf stage. The cruciferous sprouts include *Brassica oleracea* varieties *acephala, alboglabra, botrytis, costata, gemmifera, gongylodes, italica, medullosa, palmifolia, ramosa, sabauda, sabellica,* and *selensia.*

Another embodiment of the present invention provides cruciferous sprouts, with the exception of cabbage, cress, mustard and radish sprouts, harvested prior to the 2-leaf stage, wherein the sprouts are substantially free of Phase 1 enzyme-inducing potential.

Yet another embodiment of the present invention provides a non-toxic solvent extract of cruciferous sprouts, with the exception of cabbage, cress, mustard and radish sprouts, harvested prior to the 2-leaf stage. The non-toxic solvent extract can be a water extract. In addition, the water extract can comprise a cruciferous vegetable, such as a cruciferous vegetable of the genus *Raphanus*, comprising an active myrosinase enzyme.

Another embodiment of the present invention provides a food product comprising cruciferous sprouts, with the exception of cabbage, cress, mustard and radish sprouts, harvested prior to the 2-leaf stage; extracts of the sprouts or cruciferous seeds; or any combination of the sprouts or extracts.

A further embodiment of the present invention provides a method of increasing the chemoprotective amount of Phase 2 enzymes in a mammal, comprising the step of administering an effective quantity of cruciferous sprouts, with the exception of cabbage, cress, mustard and radish sprouts, harvested prior to the 2-leaf stage.

Yet another embodiment of the present invention provides a method of increasing the chemoprotective amount of Phase 2 enzymes in a mammal, comprising the step of administering an effective quantity of a food product comprising cruciferous sprouts, with the exception of cabbage, cress, mustard and radish sprouts, harvested prior to the 2-leaf stage.

Another embodiment of the present invention provides cruciferous sprouts harvested prior to the 2-leaf stage, wherein the sprouts have at least 200,000 units per gram fresh weight of Phase 2 enzyme-inducing potential when measured after 3 days of growth from seeds that produce said sprouts and contain non-toxic levels of indole glucosinolates and their breakdown products and goitrogenic hydroxybutenyl glucosinolates. The cruciferous sprouts include *Brassica oleracea* varieties *acephala, alboglabra, botrytis, costata, gemmifera, gongylodes, italica, medullosa, palmifolia, ramosa, sabauda, sabellica,* and *selensia.*

A further embodiment of the present invention provides a food product comprising sprouts harvested prior to the 2-leaf stage, wherein the sprouts have at least 200,000 units per gram fresh weight of Phase 2 enzyme-inducing potential when measured after 3 days from growth of seeds that produce the sprouts and contain non-toxic levels of indole glucosinolates and their breakdown products and goitrogenic hydroxybutenyl glucosinolates; extracts of the sprouts or cruciferous seeds; or any combination of the sprouts or extracts.

Yet another embodiment of the present invention provides cruciferous sprouts harvested prior to the 2-leaf stage, wherein the sprouts have at least 200,000 units per gram fresh weight of Phase 2 enzyme-inducing potential when measured after 3 days of growth from seeds that produce the sprouts and contain non-toxic levels of indole glucosinolates and their breakdown products and goitrogenic hydroxybutenyl glucosinolates and are substantially free of Phase 1 enzyme-inducing potential.

Another embodiment of the present invention provides a non-toxic solvent extract of cruciferous sprouts harvested prior to the 2-leaf stage, wherein the sprouts have at least 200,000 units per gram fresh weight of Phase 2 enzyme-inducing potential when measured after 3 days of growth from seeds that produce the sprouts and contain non-toxic levels of indole glucosinolates and their breakdown products and goitrogenic hydroxybutenyl glucosinolates. The non-toxic solvent extract can be a water extract. In addition, the water extract can comprise a cruciferous vegetable, such as a cruciferous vegetable of the genus *Raphanus*, comprising an active myrosinase enzyme.

Yet another embodiment of the present invention provides a method of increasing the chemoprotective amount of Phase 2 enzymes in a mammal, comprising the step of administering an effective quantity of cruciferous sprouts harvested prior to the 2-leaf stage, wherein the sprouts have at least 200,000 units per gram fresh weight of Phase 2 enzyme-inducing potential when measured after 3 days of growth from seeds that produce the sprouts and contain non-toxic levels of indole glucosinolates and their breakdown products and goitrogenic hydroxybutenyl glucosinolates.

Yet another embodiment of the present invention provides a method of increasing the chemoprotective amount of Phase 2 enzymes in a mammal, comprising the step of administering an effective quantity of a food product comprising sprouts harvested prior to the 2-leaf stage, wherein the sprouts have at least 200,000 units per gram fresh weight of Phase 2 enzyme-inducing potential when measured after 3 days of growth from seeds that produce the sprouts and contain non-toxic levels of indole glucosinolates and their breakdown products and goitrogenic hydroxybutenyl glucosinolates.

A further embodiment of the present invention provides a method of preparing a food product rich in glucosinolates, comprising germinating cruciferous seeds, with the exception of cabbage, cress, mustard and radish seeds, and harvesting sprouts prior to the 2-leaf stage to form a food product comprising a plurality of sprouts. The cruciferous sprouts include *Brassica oleracea* varieties acephala, alboglabra, botrytis, costata, gemmifera, gongylodes, italica, medullosa, palmifolia, ramosa, sabauda, sabellica, and selensia and contain non-toxic levels of indole glucosinolates and their breakdown products and goitrogenic hydroxybutenyl glucosinolates.

Yet another embodiment of the present invention provides a food product rich in glucosinolates made by germinating cruciferous seeds, with the exception of cabbage, cress, mustard and radish seeds, and harvesting sprouts prior to the 2-leaf stage to form a food product comprising a plurality of sprouts.

Yet another embodiment of the present invention provides a method of preparing a food product comprising extracting glucosinolates and isothiocyanates from cruciferous sprouts, with the exception of cabbage, cress, mustard and radish sprouts, harvested prior to the 2-leaf stage, with a non-toxic solvent and recovering the extracted glucosinolates and isothiocyanates. Myrosinase enzyme, or a vegetable, such as Raphanus species, containing the enzyme is mixed with the cruciferous sprouts, the extract, or both the sprouts and the extract.

An embodiment of the present invention provides a method of preparing a food product rich in glucosinolates, comprising germinating cruciferous seeds having at least 200,000 units per gram fresh weight of Phase 2 enzyme-inducing potential when measured after 3 days of growth from seeds that produce the sprouts and which contain non-toxic levels of indole glucosinolates and their breakdown products and goitrogenic hydroxybutenyl glucosinolates, and harvesting sprouts prior to the 2-leaf stage to form a food product comprising a plurality of sprouts. The seeds may be *Brassica oleracea*, including the varieties acephala, albogabra, botrytis, costata, gemnifera, gongylodes, italica, medullosa, palmifolia, ramosa, sabauda, sabellica, and selensia.

Yet another embodiment of the present invention provides a food product rich in glucosinolates made by germinating cruciferous seeds having at least 200,000 units per gram fresh weight of Phase 2 enzyme-inducing potential when measured after 3 days of growth from seeds that produce the sprouts and which contain non-toxic levels of indole glucosinolates and their breakdown products and goitrogenic hydroxybutenyl glucosinolates, and either harvesting sprouts at the 2-leaf stage to form a food product comprising a plurality of sprouts. The nutritional product contains non-toxic levels of indole glucosinolates and their breakdown products and goitrogenic hydroxybutenyl glucosinolates.

A further embodiment of the present invention provides a method of preparing a food product comprising extracting glucosinolates and isothiocyanates with a solvent from cruciferous seeds, sprouts, plants or plant parts, wherein seeds that produce the sprouts, plants or plant parts producing sprouts having at least 200,000 units per gram fresh weight of Phase 2 enzyme-inducing potential when measured after 3 days of growth and wherein the seeds, sprouts, plants or plant parts have non-toxic levels of indole glucosinolates and their breakdown products and goitrogenic hydroxybutenyl glucosinolates, and recovering the extracted glucosinolates and isothiocyanates. The non-toxic extraction solvent can be water. Myrosinase enzyme, or a vegetable, such as *Raphanus* species, containing the enzyme is mixed with the cruciferous sprouts, seeds, plants, plant parts or extract, or any combination thereof.

A further embodiment of the present invention provides a method of reducing the level of carcinogens in mammals, comprising administering cruciferous sprouts, with the exception of cabbage, cress, mustard and radish sprouts.

Yet another embodiment of the present invention provides a method of reducing the level of carcinogens in mammals, comprising administering cruciferous sprouts having at least 200,000 units per gram fresh weight of Phase 2 enzyme-inducing potential when measured after 3 days of growth from seeds that produce the sprouts and non-toxic levels of indole glucosinolates and their breakdown products and goitrogenic hydroxybutenyl glucosinolates.

Another embodiment of the present invention provides a method of preparing a food product by introducing cruciferous seeds, having at least 200,000 units per gram fresh weight of Phase 2 enzyme-inducing potential when measured after 3 days of growth from seeds that produce the sprouts and non-toxic levels of indole glucosinolates and goitrogenic hydroxybutenyl glucosinolates, into an edible ingredient.

A further embodiment of the present invention provides a method of extracting glucosinolates and isothiocyanates from plant tissue which comprises homogenizing the plant tissue in an excess of a mixture of dimethyl sulfoxide, acetonitrile, and dimethylformamide (DMF/ACN/DMSO) at a temperature that prevents myrosinase activity.

Another embodiment of the present invention provides cruciferous sprouts harvested prior to the 2-leaf stage, wherein the ratio of monofunctional to bifunctional inducers is at least 20 to 1.

Another object of the present invention is to provide a food product supplemented with a purified or partially purified glucosinolate.

Other objects, features and advantages of the present invention will become apparent from the following detailed description. It should be understood, however, that the detailed description and the specific examples, while indicating preferred embodiments of the invention, are given by way of illustration only, since various changes and modifications within the spirit and scope of the invention will become apparent to those skilled in the art from this detailed description.

DETAILED DESCRIPTION

I. Definitions

Figure 1:
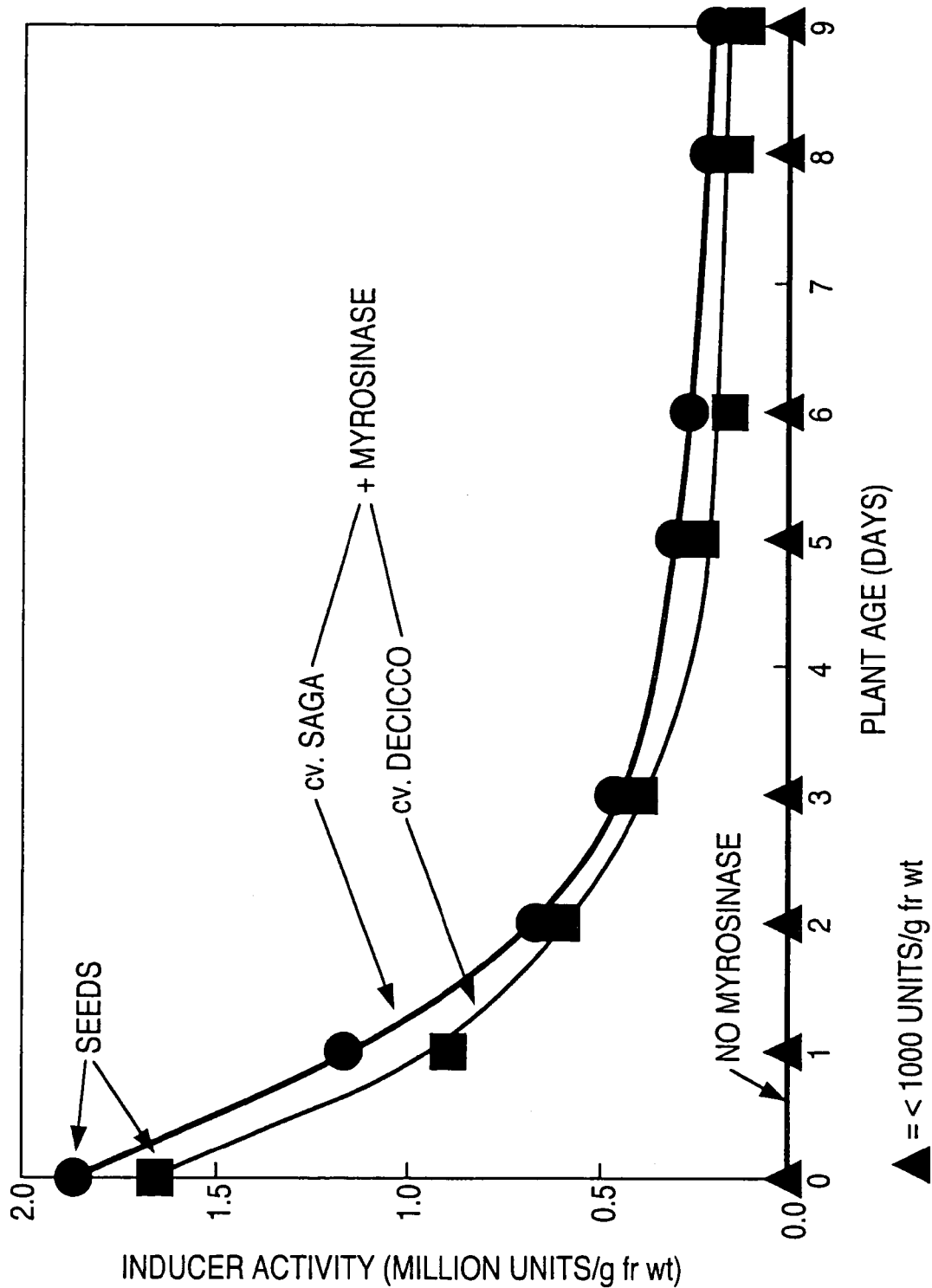
FIG. 1 shows the total inducing potential of organic solvent extracts of broccoli and daikon cultivars as a function of age.

In the description that follows, a number of terms are used extensively. The following definitions are provided to facilitate understanding of the invention.

A bifunctional inducer is a molecule which increases activities of both Phase 1 enzymes such as cytochromes P-450 and Phase 2 enzymes and requires the participation of Aryl hydrocarbon (Ah) receptor and its cognate Xenobiotic Response Element (XRE). Examples include flat planar aromatics such as polycyclic hydrocarbons, azo dyes or 2,3,7,8-tetrachloro-dibenzo-p-dioxin (TCDD).

A chemoprotector or chemoprotectant is a synthetic or naturally occurring chemical agent that reduces susceptibility in a mammal to the toxic and neoplastic effects of carcinogens.

A food product is any ingestible preparation containing the sprouts of the instant invention, or extracts or preparations made from these sprouts, which are capable of delivering Phase 2 inducers to the mammal ingesting the food product. The food product can be freshly prepared such as salads, drinks or sandwiches containing sprouts of the instant invention. Alternatively, the food product containing sprouts of the instant invention can be dried, cooked, boiled, lyophilized or baked. Breads, teas, soups, cereals, pills and tablets, are among the vast number of different food products contemplated.

Inducer activity or Phase 2 enzyme-inducing activity is a measure of the ability of a compound(s) to induce Phase 2 enzyme activity. In the present invention, inducer activity is measured by means of the murine hepatoma cell bioassay of QR activity in vitro. Inducer activity is defined herein as QR inducing activity in Hepa 1c1c7 cells (murine hepatoma cells) incubated with extracts of sprouts, seeds or other plant parts untreated with myrosinase. Inducer activity is measured in Hepa 1c1c7 murine hepatoma cells grown in 96-well microtiter plates. Typically 10,000 Hepa 1c1c7 cells are introduced into each well. Hepatoma cells are grown for 24 hours and a plant extract containing microgram quantities of fresh plant tissue is serially diluted across the microtiter plates into fresh culture medium containing 0.15 ml αMEM culture medium amended with 10% Fetal Calf Serum (FCS) and streptomycin and penicillin. The cells are further incubated for 48 hours. QR activity (based on the formation of the blue-brown reduced tetrazolium dye) is measured with an optical microtiter plate scanner in cell lysates prepared in one plate, and related to its protein concentration. Quantitative information on specific activity of QR is obtained by computer analysis of the absorbances. One unit of inducer activity is the amount that when added to a single microtiter well doubles the QR activity. (See Prochaska and Santamaria, *Anal. Biochem.* 169: 328-336 (1988) and Prochaska et al., *Proc. Natl. Acad. Sci. USA* 89: 2394-2398 (1992)).

Inducer potential or Phase 2 enzyme-inducing potential is a measure of the combined amounts of inducer activity in plant tissue provided by isothiocyanates, plus glucosinolates that can be converted by myrosinase to isothiocyanates. Glucosinolates are not themselves inducers of mammalian Phase 2 enzymes, whereas isothiocyanates are inducers. Inducer potential therefore is defined herein as QR activity in murine 1c1c7 hepatoma cells incubated with myrosinase-treated extracts of the sprouts, seeds or other plant parts. In the present invention therefore inducer potential is measured by means of the murine hepatoma cell bioassay of QR activity in vitro as described above. Inducer potential is measured in Hepa 1c1c7 murine hepatoma cells grown in 96-well microtiter plates. Typically, 10,000 Hepa 1c1c7 cells are introduced into each well. Hepatoma cells are grown for 24 hours and a plant extract containing microgram quantities of fresh plant tissue is serially diluted across the microtiter plates into fresh culture medium containing 0.15 ml αMEM culture medium amended with 10% Fetal Calf Serum (FCS) and streptomycin and penicillin. Myrosinase (6 units/ml plant extract) is added to the plant extract. Myrosinase is purified by modification of the technique of Palmieri et al., *Anal. Biochem.* 35: 320-324 (1982) from 7 day old Daikon sprouts grown on agar support containing no added nutrients. Following 234-fold purification, the myrosinase had a specific activity of 64 units/mg protein [unit=amount of enzyme required to hydrolyze 1 μmol sinigrin/min]. Plant extract is diluted 200-fold into the initial wells of the microtiter plate followed by 7 serial dilutions. The cells are further incubated for 48 hours. QR activity (based on the formation of the blue-brown reduced tetrazolium dye) is measured with an optical microtiter plate scanner in cell lysates prepared in one plate, and related to its protein concentration. Quantitative information on specific activity of QR is obtained by computer analysis of absorbances. One unit of inducer potential is the amount that when added to a single microtiter well doubles the QR activity. (See Prochaska and Santamaria, *Anal. Biochem.* 169: 328-336 (1988) and Prochaska et al., *Proc. Natl. Acad. Sci. USA* 89: 2394-2398 (1992)).

A monofunctional inducer increases the activity of Phase 2 enzymes selectively without significantly altering Phase 1 enzyme activities. Monofunctional inducers do not depend on a functional Ah receptor but enhance transcription of Phase 2 enzymes by means of an Antioxidant Responsive Element (ARE).

A cruciferous sprout is a plant or seedling that is at an early stage of development following seed germination. Cruciferous seeds are placed in an environment in which they germinate and grow. The cruciferous sprouts of the instant invention are harvested following seed germination through and including the 2-leaf stage. The cruciferous sprouts of instant invention have at least 200,000 units per gram fresh weight of Phase 2 enzyme-inducing potential at 3-days following incubation under conditions in which cruciferous seeds germinate and grow.

II. Description

A major mechanism of protection provided by fruits and vegetables in reducing the cancer incidence in humans depends on minor chemical components which, when delivered to mammalian cells, elevate levels of Phase 2 enzymes that detoxify carcinogens. It has now been discovered that the anticarcinogenic activity of certain edible plants can be increased. Plants such as *Brassica oleracea* variety italica (broccoli) are normally not harvested until they form heads. By growing these plants only to the seedling or sprout stage, that is between the onset of germination and the 2-leaf stage, the levels of inducers of enzymes that detoxify carcinogens and protect against cancer can be increased at least five-fold over those found in commercial stage vegetables of the same cultivars. Often increases of between 10 and 1000-fold have been observed.

Harvesting plants at an early seedling or sprout stage, or otherwise arresting their growth, leads to the greatest inducer potential and yields a food product of a type to which consumers are already accustomed. The Phase 2 enzyme-inducing potential of such sprouts may be as much as several hundred times higher than that observed in adult, market stage vegetables obtained from the same seeds. Thus it is possible that humans can consume the same quantities of inducer potential by eating relatively small quantities of sprouts, rather than large quantities of market-stage vegetables.

It has now been found that most of the inducer potential of crucifer plants is due to their content of isothiocyanates and their biogenic precursors, glucosinolates. Glucosinolates are converted to isothiocyanates by the enzyme myrosinase which is a thioglucosidase. Normally myrosinase and glucosinolates are separated in the cell and if the cell is damaged, with loss of compartmentalization, myrosinase comes into contact with glucosinolates, which are then converted to isothiocyanates.

In order to screen large numbers of edible plants and to evaluate the effects of environmental perturbation on Phase 2 enzyme-inducer potential in those vegetables, it was necessary to improve upon the previously described techniques for homogenization and extraction of those vegetables. Techniques initially described for the extraction of Phase 2 inducers from vegetables involved homogenization of the vegetables in cold water, lyophilization, extraction of the resultant powder with acetonitrile, filtration and evaporative concentration, Prochaska et al., *Proc. Natl. Acad. Sci. USA* 89: 2394-2398 (1992).

Following identification of sulforaphane as the principal Phase 2 inducer from broccoli, comparative extractions were performed into hot 80% methanol, yielding similar inducer activity as the aforementioned acetonitrile extracts. When myrosinase was added to these hot methanol extracts in which glucosinolates are freely soluble, there was a dramatic enhancement of the Phase 2 inducer activity of these extracts (data summarized in Table 1). The deliberate conversion of these glucosinolates to isothiocyanates using exogenous myrosinase thus gave a better index of the inducers for Phase 2 enzymes of the vegetables tested. It was thus clear that the majority of the potential Phase 2 inducers in crucifers was usually present in whole plants as the glucosinolate precursors of isothiocyanates.

The preponderance of glucosinolates and the rapidity with which, upon wounding of cruciferous plant tissue, glucosinolates are converted to isothiocyanates, led to the development of an improved extraction procedure. By manipulation of solvent mixtures and of the water activity of fresh vegetable/solvent homogenates, a procedure was developed that permits both glucosinolate and isothiocyanate quantification from the same, non-concentrated sample. In addition to being the rate-limiting step in an extraction protocol, evaporative concentration allows volatile inducers to escape detection. The improved procedure is both simple and efficient, requiring only that the plant sample be completely homogenized in solvent. Using this technique, the present inventors have thus been able to demonstrate dramatic increases in the recovery of inducer activity and inducer potential from cruciferous vegetables over previously described techniques.

If fresh-picked vegetables are promptly and gently harvested, directly into organic solvents comprising a mixture of DMF/ACN/DMSO and a temperature that prevents myrosinase activity, both glucosinolates and isothiocyanates are efficiently extracted into the organic solvent mixture. Preferably, the DMF, ACN and DMSO are mixed in equal volumes. However, the volumes of the three solvents in the mixture can be varied to optimize extraction of specific glucosinolates and isothiocyanates from any plant tissue. The temperature of the extraction mixture is preferably less than 0° C., and most preferably less than −50° C. The temperature of the extraction solvent must be kept above freezing. At the same time the enzyme myrosinase, which invariably accompanies these constituents in the plants and rapidly converts glucosinolates into isothiocyanates, is inactive. Such extracts typically contain high quantities of glucosinolates and negligible quantities of isothiocyanates. The in planta myrosinase activity varies between different plant species.

Glucosinolates are not themselves inducers of mammalian Phase 2 enzymes, whereas isothiocyanates are monofunctional inducers in the murine hepatoma cell bioassay of QR activity. The inducer potential, as distinct from inducer activity, of plant extracts can be measured by adding purified myrosinase, obtained from the same, or other plant sources, to the assay system.

Glucosinolates are converted at least partially to isothiocyanates in humans. If, however, it is desirable to accelerate this conversion, broccoli or other vegetable sprouts, high in glucosinolates, can be mixed with myrosinase. The mixture can be in water, or some other non-toxic solvent that does not inactivate myrosinase. The myrosinase can be from a partially purified or purified preparation. Alternatively, the myrosinase can be present in plant tissue, such as a small quantity of crucifer sprouts rich in myrosinase, including *Raphanus sativus* or daikon. Such a preparation can be used to produce a "soup" for ingestion that is high in isothiocyanates and low in glucosinolates. Inducer potential can be measured using a multiwell plate screen with murine hepatoma cells for in vitro measurement of QR specific activity as described above.

The ratio of monofunctional to bifunctional inducer activity of plant tissue is measured by bioassaying plant extracts, as described above, not only in wild-type Hepa 1c1c7 cells, but also, in mutants designated c1 and BP$^r$c1 that have either defective Ah receptors or defective cytochrome $P_1$-450 genes, respectively. Prochaska and Talalay, *Cancer Research* 48: 4776-4782 (1988).

A harvested sprout according to the present invention can be incorporated immediately into food products such as fresh salads, sandwiches or drinks. Alternatively, the growth of the harvested sprout can be arrested by some active human intervention, for example by refrigeration, at a stage of growth prior to the 2-leaf stage, typically between 1 and 14 days after germination of seeds. Growth arrest can also be accomplished by removing a sprout from its substrate and/or water source. Freezing, drying, baking, cooking, lyophilizing and boiling are among the many treatments that can be used to arrest growth. These may also be useful for either preserving myrosinase activity in the sprout (e.g., lyophilizing) or for inactivating myrosinase activity in the sprout (e.g., boiling), as is desired in a particular application.

The harvested sprout can also be allowed to mature further, under different growing conditions, prior to incorporation into a food product. For example, the sprout can be harvested at a very young age of development, such as 1 to 2 days after seed imbibition. The sprout can then be allowed to mature under different growing conditions, such as increased or decreased light intensity, temperature or humidity; exposure to ultraviolet light or other stresses; or addition of exogenous nutrients or plant growth regulators (hormones). The sprout is then immediately incorporated into a food product, such as for fresh consumption in salads. Alternatively, the growth of the sprout is arrested and/or further treated by means of lyophilization, drying, extracting with water or other solvents, freezing, baking, cooking, or boiling, among others.

A sprout is suitable for human consumption if it does not have non-edible substrate such as soil attached or clinging to it. Typically the sprouts are grown on a non-nutritive solid support, such as agar, paper towel, blotting paper, Vermiculite, Perlite, etc., with water and light supplied. Thus, if a sprout is not grown in soil, but on a solid support, it does not need to be washed to remove non-edible soil. If a sprout is grown in a particulate solid support, such as soil, Vermiculite, or Perlite, washing may be required to achieve a sprout suitable for human consumption.

Sprouts can be grown in containers which are suitable for shipping and marketing. Typically such containers are plastic boxes or jars which contain a wetted pad at the bottom. The containers allow light to penetrate while providing a mechanically protective barrier. Numerous methods for the cultivation of sprouts are known, as exemplified by U.S. Pat. Nos. 3,733,745, 3,643,376, 3,945,148, 4,130,964, 4,292,760 or 4,086,725. Food products containing the sprouts of the instant invention can be stored and shipped in diverse types of containers such as jars, bags and boxes, among many others.

Sprouts suitable as sources of cancer chemoprotectants are generally cruciferous sprouts, with the exception of cabbage (*Brassica oleracea capitata*), cress (*Lepidiumsativum*), mustard (*Sinapis alba* and *S. niger*) and radish (*Raphanus sativus*) sprouts. The selected sprouts are typically from the family Cruciferae, of the tribe *Brassiceae*, and of the subtribe Brassicinae. Preferably the sprouts are *Brassica oleracea* selected from the group of varieties consisting of acephala (kale, collards, wild cabbage, curly kale), medullosa (marrowstem kale), ramosa (thousand head kale), alboglabra (Chinese kale), *botrytis* (cauliflower, sprouting broccoli), costata (Portuguese kale), gemmifera (Brussels sprouts), gongylodes (kohlrabi), italica (broccoli), palmifolia (Jersey kale), sabauda (savoy cabbage), sabellica (collards), and selensia (borecole), among others.

Particularly useful broccoli cultivars to be used in the claimed method are Saga, DeCicco, Everest, Emerald City, Packman, Corvet, Dandy Early, Emperor, Mariner, Green Comet, Green Valiant, Arcadia, Calabrese Caravel, Chancellor, Citation, Cruiser, Early Purple Sprouting Red Arrow, Eureka, Excelsior, Galleon, Ginga, Goliath, Green Duke, Greenbelt, Italian Sprouting, Late Purple Sprouting, Late Winter Sprouting White Star, Legend, Leprechaun, Marathon, Mariner, Minaret (Romanesco), Paragon, Patriot, Premium Crop, Rapine (Spring Raab), Rosalind, Salade (Fall Raab), Samurai, Shogun, Sprinter, Sultan, Taiko, and Trixie. However, many other broccoli cultivars are suitable.

Particularly useful cauliflower cultivars are Alverda, Amazing, Andes, Burgundy Queen, Candid Charm, Cashmere, Christmas White, Dominant, Elby, Extra Early Snowball, Fremont, Incline, Milkyway Minuteman, Rushmore, S-207, Serrano, Sierra Nevada, Siria, Snow Crown, Snow Flake, Snow Grace, Snowbred, Solide, Taipan, Violet Queen, White Baron, White Bishop, White Contessa, White Corona, White Dove, White Flash, White Fox, White Knight, White Light, White Queen, White Rock, White Sails, White Summer, White Top, Yukon. However, many other cauliflower cultivars are suitable.

Suitable sprouts will have at least 200,000 units per gram of fresh weight of Phase 2 enzyme-inducing potential following 3-days incubation of seeds under conditions in which the seeds germinate and grow. Preferably the sprouts will have at least 250,000 units of inducer potential per gram of fresh weight, or even 300,000 units, 350,000 units, 400,000 units, or 450,000 units. Some samples have been found to contain greater than 500,000 units per gram of fresh weight at 3-days of growth from seeds.

The level of inducing activity and inducing potential has been found to vary among crucifers and even among cultivars. Most preferably, the sprouts are substantially free of indole glucosinolates and their breakdown products which have Phase 1 enzyme-inducing potential in mammalian cells, and substantially free of toxic levels of goitrogenic nitriles and glucosinolates such as hydroxybutenyl glucosinolates, which upon hydrolysis yield oxazolidonethiones which are goitrogenic. Mature Brussels sprouts and rapeseed are rich in these undesirable glucosinolates.

Non-toxic solvent extracts according to the invention are useful as healthful infusions or soups. Non-toxic or easily removable solvents useful for extraction according to the present invention include water, liquid carbon dioxide or ethanol, among others. The sprouts can be extracted with cold, warm, or preferably hot or boiling water which denature or inactivate myrosinase. The residue of the sprouts, post-extraction, may or may not be removed from the extract. The extraction procedure may be used to inactivate myrosinase present in the sprouts. This may contribute to the stability of the inducer potential. The extract can be ingested directly, or can be further treated. It can, for example, be evaporated to yield a dried extracted product. It can be cooled, frozen, or freeze-dried. It can be mixed with a crucifer vegetable which contains an active myrosinase enzyme. This will accomplish a rapid conversion of the glucosinolates to isothiocyanates, prior to ingestion. Suitable vegetables that contain active myrosinase are of the genus *Raphanus*, especially daikon, a type of radish.

Seeds, as well as sprouts have been found to be extremely rich in inducer potential. Thus it is within the scope of the invention to use crucifer seeds in food products. Suitable crucifer seeds may be ground into a flour or meal for use as a food or drink supplement. The flour or meal is incorporated into breads, other baked goods, or health drinks or shakes. Alternatively, the seeds may be extracted with a non-toxic solvent such as water, liquid carbon dioxide or ethanol to prepare soups, teas or other drinks and infusions. The seeds can also be incorporated into a food product without grinding. The seeds can be used in many different foods such as salads, granolas, breads and other baked goods, among others.

Food products of the instant invention may include sprouts, seeds or extracts of sprouts or seeds taken from one or more different crucifer genera, species, varieties, subvarieties or cultivars. It has been found that genetically distinct crucifers produce chemically distinct Phase 2 enzyme-inducers. Different Phase 2 enzyme-inducers detoxify chemically distinct carcinogens at different rates. Accordingly, food products composed of genetically distinct crucifer sprouts or seeds, or extracts or preparations made from these sprouts or seeds, will detoxify a broader range of carcinogens.

Glucosinolates and/or isothiocyanates can be purified from seed or plant extracts by methods well known in the art. See Fenwick et al., *CRC Crit. Rez. Food Sci. Nutr.* 123-201 (1983) and Zhang et al., *Pro. Natl Acad. Sci. USA* 89: 2399-2403 (1992). Purified or partially purified glucosinolate(s) or isothiocyanate(s) can be added to food products as a supplement. The dose of glucosinolate and/or isothiocyanate added to the food product preferably is in the range of 1 μmol to 1,000 μmols. However, the dose of glucosinolate and/or isothiocyanate supplementing the food product can be higher.

The selection of plants having high Phase 2 enzyme-inducer potential in sprouts, seeds or other plant parts can be incorporated into Cruciferae breeding programs. In addition, these same breeding programs can include the identification and selection of cultivars that produce specific Phase 2 enzyme-inducers, or a particular spectrum of Phase 2 enzyme-inducers. Strategies for the crossing, selection and breeding of new cultivars of Cruciferae are well known to the skilled artisan in this field. *Brassica Crops and Wild Allies: Biology & Breeding*; S. Tsunoda et al. (eds), Japan Scientific Societies Press, Tokyo pp. 354 (1980). Progeny plants are screened for Phase 2 inducer activity or the chemical identity of specific Phase 2 enzyme-inducers produced at specific plant developmental stages. Plants carrying the trait of interest are identified and the characteristic intensified or combined with other important agronomic characteristics using breeding techniques well known in the art of plant breeding.

EXAMPLE 1

Comparison of Cruciferous Sprout Inducing Potential

Sprouts were prepared by first surface sterilizing seeds of different species from the cruciferae family with a 1 min treatment in 70% ethanol, followed by 15 min in 1.3% sodium hypochlorite containing approximately 0.001% Alconox detergent. Seeds were grown in sterile plastic containers at a density of approximately 8 seeds/cm$^2$ for from 1 to 9 days on a 0.7% agar support that did not contain added nutrients. The environment was carefully controlled with broad spectrum fluorescent lighting, humidity and temperature control. The seeds and sprouts were incubated under a daily cycle of 16 hours light at 25° C. and 8 hours dark at 20° C.

Sprouts were harvested following 3-days of incubation and immediately plunged into 10 volumes of a mixture of equal volumes of DMF/ACN/DMSO at –50° C. This solvent mixture has a freezing point of approximately –33° C., but when admixed with 10% water, as found in plant material, the freezing point is depressed to below –64° C. The actual freezing point depression is even greater with plant material.

Homogenization was accomplished either by manually grinding the samples in a glass-on-glass homogenizer in the presence of a small amount of the total solvent used, then gradually adding more solvent or homogenizing the sample in 10 volumes of solvent using a Brinkman Polytron Homogenizer for 1 min at half-maximum power. The homogenate was then centrifuged to remove remaining particulates and stored at –20° C. until assayed.

Inducer potential of plant extracts prepared as described above, was determined by the microtiter plate bioassay method as described in the Definitions section above.

Broccoli and cauliflower sprouts harvested and assayed at 3-days after incubation of seeds under growth conditions have Phase 2 enzyme-inducer potential greater than 200,000 units/g fresh weight. On the other hand, cabbage, radish, mustard and cress have Phase 2 enzyme-inducer potential of less than 200,000 units/g fresh weight when assayed at the same time point.

EXAMPLE 2

Variation in Inducer Potential Among Differ Broccoli Cultivars

There is variation in inducer potential among different broccoli cultivars. In addition, most of the inducer potential in crucifers is present as precursor glucosinolates. The inducer activity and inducer potential of market stage broccoli heads was determined following DMF/ACN/DMSO extractions and assay of QR activity as described above.

Bioassay of homogenates of such market stage broccoli heads, with and without the addition of purified plant myrosinase, showed that the amount of QR activity found in the absence of myrosinase was less than 5% of that observed with added myrosinase. These observations confirmed previous suggestions (see Matile et al., *Biochem. Physiol. Pflanzen* 179: 5-12 (1984)) that uninjured plants contain almost no free isothiocyanates.

TABLE 1

Effect of Myrosinase on Inducer Activity of Market-Stage Broccoli Plant Heads

| Broccoli cultivar | Units per gram (wet weight) vegetable | |
| --- | --- | --- |
| | − myrosinase | + myrosinase |
| DeCicco | 5,882 | 37,037 |
| Calabrese Corvet | 1,250 | 41,666 |
| Everest | * | 8,333 |
| Dandy Early | * | 20,000 |
| Emperor | * | 13,333 |
| Saga | 5,000 | 13,333 |
| Emerald City | * | 12,500 |

* Below limits of detection (833 units/g).

As can be observed in Table 1, most of the plant inducer potential is derived from glucosinolates following hydrolysis by myrosinase to form isothiocyanates. Hence, hydrolysis is required for biological activity.

EXAMPLE 3

Inducer Potential is Highest in Seeds and Decreases as Sprouts Mature

Phase 2 enzyme-inducer potential is highest in seeds and decrease gradually during early growth of seedlings. Plants were prepared by first surface sterilizing seeds of *Brassica oleracea* variety italica cultivars Saga and DeCicco with a 1 min treatment in 70% ethanol, followed by 15 min in 1.3% sodium hypochlorite containing approximately 0.001% Alconox detergent. Seeds were grown in sterile plastic containers at a density of approximately 8 seeds/cm$^2$ on a 0.7% agar support that did not contain added nutrients. The environment was carefully controlled with broad spectrum fluorescent lighting, humidity and temperature control. The seeds and sprouts were incubated under a daily cycle of 16 hours light at 25° C. and 8 hours dark at 20° C.

Each day plants were rapidly and gently collected from the surface of the agar from replicate containers. The plants were harvested gently to minimize glucosinolate hydrolysis by endogenous myrosinase released upon plant wounding. Samples containing approximately 40 sprouts were homogenized in 10 volumes of DMF/ACN/DMSO solvent at −50° C. which dissolves nearly all the non-lignocellulosic plant material.

Harvested plants were homogenized and QR activity with and without myrosinase, was determined as described above. As can be seen in FIG. 1, Phase 2 enzyme-inducer potential per gram of plant is highest in seeds, but decreases gradually following germination. No detectable (less than 1000 units/g) QR inducer activity was present in the absence of added myrosinase.

EXAMPLE 4

Sprouts Have Higher Inducer Potential Than Market Stage Plants

The cruciferous sprouts of the instant invention have higher Phase 2 enzyme-inducer potential than market stage plants. More specifically, sprouts have at least a 5-fold greater Phase 2 enzyme-inducing potential than mature vegetables. For example, total inducing potential of 7-day-old broccoli sprouts, extracted with DMF/ACN/DMSO and treated with myrosinase, as described above, were 238,000 and 91,000 units/g fresh weight, compared to 25,000 and 20,000 units/g fresh weight for field-grown heads of broccoli cultivars Saga and DeCicco, respectively.

Sprout extracts of over 40 different members of the Cruciferae have now been bioassayed and broccoli sprouts remain the most Phase 2 enzyme-inducer-rich plants tested. Total inducing potential of organic solvent extracts of market stage and sprout stage broccoli and daikon is shown in Table 2.

TABLE 2

Comparison of Inducer Potential in Sprouts and Mature Vegetables

| | Activity (units/g fresh weight) | | |
| --- | --- | --- | --- |
| Vegetable Cultivar* | Mature Vegetable | Sprout** | − Fold Difference |
| DAIKON | | | |
| Miura | 625 | 26,316 | 42 |
| Tenshun | 3,333 | 33,333 | 10 |
| Hakkai | 1,471 | 16,667 | 11 |
| Ohkura | 2,857 | 50,000 | 18 |
| BROCCOLI | | | |
| Saga | 25,000 | 476,000 | 19 |
| DeCicco | 25,000 | 625,000 | 25 |
| Everest | 8,333 | 1,087,000 | 130 |
| Emerald City | 12,500 | 833,000 | 67 |
| Packman | 20,000 | 556,000 | 28 |

*The commercial portion of each plant was sampled (e.g. the taproot of *Raphanus sativus* variety *radicola* [radish]), and heads of *Brassicsa oleracea* variety *izalica* [broccoli]). Myrosinase was added to all extracts tested.
**Broccoli sprouts were 1-day old and daikon seedlings were 4-5-days old.

Sprouts of the broccoli cultivar Everest contained 130-fold more inducer potential (units/g fresh weight) than mature vegetables. The inducer activity in broccoli was significantly higher than in daikon.

EXAMPLE 5

Inducer Potential of Broccoli Sprout Extracts

Inducer potential of a series of water extracts of 3-day old broccoli sprouts of the cultivar Saga were determined. Plants were prepared by first surface sterilizing seeds of *Brassica oleracea* variety italica (broccoli) cultivar Saga by a 1 min treatment in 70% ethanol, followed by 15 min in 1.3% sodium hypochlorite containing approximately 0.001% Alconox detergent. Seeds were grown in sterile plastic containers at a density of approximately 8 seeds/cm$^2$ for 72 hours on a 0.7% agar support that did not contain added nutrients. The environment was carefully controlled with broad spectrum fluorescent lighting, humidity and temperature control (16 hours light, 25° C./8 hours dark, 20° C.).

Plants were rapidly and gently collected from the surface of the agar to minimize glucosinolate hydrolysis by endogenous myrosinase released upon plant wounding. Sprouts (approximately 25 mg fresh wt/sprout) were gently harvested and immediately and rapidly plunged into approximately 3 volumes of boiling water in order to inactivate endogenous myrosinase as well as to extract glucosinolates and isothiocyanates from the plant tissue. Water was returned to a boil and maintained at a rolling boil for 3 min. The sprouts were then either strained from the boiled infusion [tea, soup] or homogenized in it, and the residue then removed by filtration or centrifugation.

Data in Table 3. represent both homogenates and infusions. Preparations were stored at −20° C. until assayed. Inducer potential of plant extracts, prepared as described above, was determined as described in Definitions section above.

TABLE 3

Inducer Potentials of Hot Water Extracts of 3-Day Saga Broccoli Sprouts

| EXTRACT NO. | units/g fresh weight |
|---|---|
| 1 | 500,000 |
| 2 | 370,000 |
| 3 | 455,000 |
| 4 | 333,000 |
| 5 | 435,000 |
| 6 | 333,000 |
| 7 | 625,000 |
| 8 | 250,000 |
| 9 | 313,000 |
| 10 | 357,000 |
| 11 | 370,000 |
| 12 | 370,000 |
| 13 | 217,000 |
| 14 | 222,000 |
| 15 | 1,000,000 |
| 16 | 714,000 |
| 17 | 435,000 |
| 18 | 1,250,000 |
| 19 | 263,000 |
| AVERAGE | 464,000 ± 61,600 S.E.M. |

Some variability in the amount of Phase 2 enzyme-inducer potential was detected. High levels of Phase 2 enzyme-inducer potential, however, were consistently observed.

EXAMPLE 6

Hot Water Broccoli Extracts Treated with Daikon Myrosinase

QR activity in a hot water broccoli extract increased in the presence of a vegetable source of myrosinase. An aqueous extraction of 3-day old sprouts of broccoli cultivar Saga grown on water agar, in which myrosinase was inactivated by boiling for 3 min, was divided into 6 different 150 ml aliquots. Nine-day old daikon sprouts, a rich source of the enzyme myrosinase, were added to this cooled infusion in amounts equivalent to 0, 5, 9, 17, 29 and 40% (w/w) of the broccoli. QR activity, as determined in the Definition section, of the control extracts containing 0% daikon was 26,300 units/gram fresh weight while QR activity of the extracts that had received daikon as a source of myrosinase ranged from 500,000 to 833,000 units/gram fresh weight of broccoli. Accordingly, myrosinase present in the daikon sprouts, increased the QR activity in the broccoli extract greater than 19-fold.

EXAMPLE 7

Glucoraphanin and Glucoerucin are the Predominant Glucosinolates in Hot Water Extracts of Broccoli (Cultivar Saga) Sprouts Paired Ion Chromatography (PIC).

Centrifuged hot water extracts of 3-day-old broccoli (cultivar Saga) sprouts were subjected to analytical and preparative PIC on a reverse phase C18 Partisil ODS-2 HPLC column in ACN/H$_2$O (1/1, by vol.) with tetraoctylammonium (TOA) bromide as the counter-ion. Only three well-separated peaks were detected: peak A eluted at 5.5 min, B at 11.5 min, and C at 13 min at a molar ratio [A:B:C] of ca. 2.5:1.6:1.0 (monitored by UV absorption at 235 nm), and they disappeared if the initial extracts were first treated with highly purified myrosinase. Peaks A, B, and C contained no significant inducer activity, and cyclocondensation assay of myrosinase hydrolysates showed that only Peaks A and C produced significant quantities of isothiocyanates, accounting for all the inducer activity. See Zhang et al., *Anal. Biochem.* 205: 100-107 (1992). Peak B was not further characterized. Peaks A and C were eluted from HPLC as TOA salts but required conversion to ammonium salts for successful mass spectroscopy, NMR and bioassay. The pure peak materials were dried in a vacuum centrifuge, redissolved in aqueous 20 mM NH$_4$Cl, and extracted with chloroform to remove excess TOA bromide. The ammonium salts of glucosinolates remained in the aqueous phase, which was then evaporated.

Identification of Glucosinolates.

Figure 2:
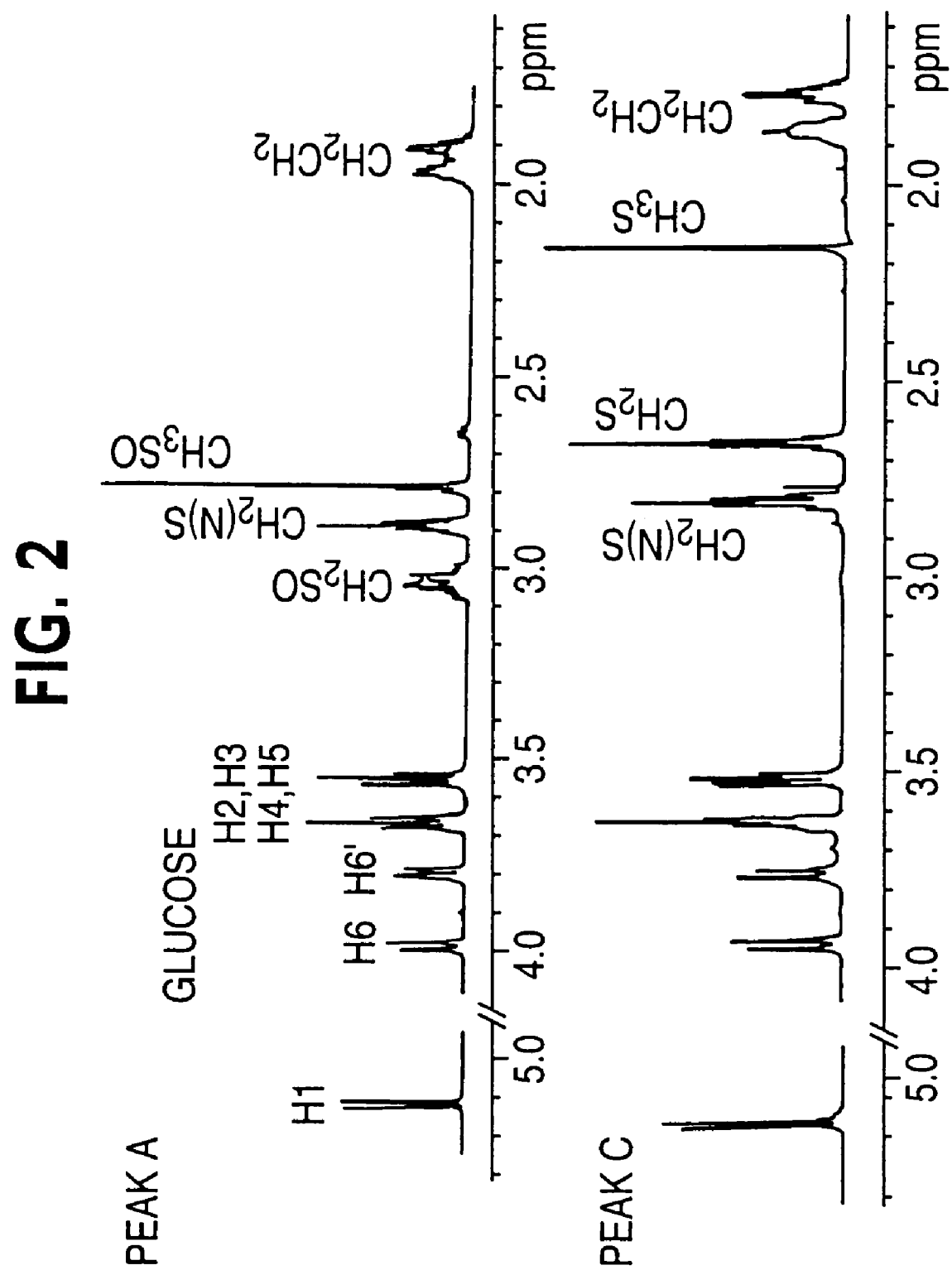
FIG. 2 shows the high resolution NMR spectra of isolated glucosinolates obtained from hot aqueous extracts of 3-day old Saga broccoli sprouts.

The ammonium salts of Peaks A and C were characterized by mass spectrometric and NMR techniques: (a) negative ion Fast Atom Bombardment (FAB) on a thioglyerol matrix; this gave values of 436 (Peak A) and 420 (Peak C) amu for the negative molecular ions, and (b) high resolution NMR, as shown in FIG. 2, provided unequivocal identification of the structure. Peak A is glucoraphanin [4-methylsulfinylbutyl glucosinolate], and Peak C is the closely related glucoerucin [4-methythiobutyl glucosinolate]. These identifications and purity are also consistent with the inducer potencies; Peaks A and C, after myrosinase hydrolysis had potencies of 36,100 and 4,360 units/μmol, respectively, compared with reported CD values of 0.2 μM (33,333 units/μmol) for sulforaphane and 2.3 μM (2,900 units/μmol) for erucin. CD values are the concentrations of a compound required to double the QR specific activity in Hepa 1c1c7 murine hepatoma cells. Since there are no other glucosinolate peaks, and the inducer activity of peak A and C account for the total inducer activity of the extracts, it is therefore likely that in this cultivar of broccoli, there are no significant quantities of other inducers, i.e., no indole or hydroxyalkenyl glucosinolates. Further, the isolated compounds are therefore substantially pure.

EXAMPLE 8

Comparison of Aqueous and Organic Solvent Techniques for Extraction of Inducer Potential Plants were prepared by first surface sterilizing seeds of Brassica oleracea variety italica (broccoli) cultivar Saga, with 70% ethanol followed by 1.3% sodium hypochlorite and 0.001% alconox. The seeds were grown in sterile plastic containers at a density of approximately 8 seeds/cm$^2$ for 72 hours on a 0.7% agar support that did not contain added nutrients. The environment was carefully controlled with broad spectrum fluorescent lighting, humidity, and temperature control (16 hours light, 25° C./8 hours dark, 20° C.).

The plants were rapidly and gently collected from the surface of the agar to minimize glucosinolate hydrolysis by endogenous myrosinase released upon plant wounding. A portion of the plants was homogenized with 10 volumes of the DMF/ACN/DMSO solvent at −50° C., as described in Example 1, which dissolves nearly all the non-lignocellulosic plant material. Alternatively, the bulk of the harvested plants was plunged into 5 volumes of boiling water for 3 min to inactivate endogenous myrosinase and to extract glucosinolates and isothiocyanates. The cooled mixture was homogenized, centrifuged, and the supernant fluid was stored at −20° C.

Inducer potential of plant extracts, prepared by the two methods described above, was determined by the microtiter plate bioassay as described above. Typical inducer potentials in-an average of 5 preparations were 702,000 (DMF/ACN/DMSO extracts) and 505,000 (aqueous extracts) units/g fresh weight of sprouts.

Spectrophotometric quantitation of the cyclocondensation product of the reaction of isothiocyanates with 1,2-benzenedithiole was carried out as described in Zhang et al., *Anal. Biochem.* 205: 100-107 (1992). Glucosinolates were rapidly converted to isothiocyanates after addition of myrosinase. About 6% of the total hot water extractable material [dissolved solids] consisted of glucosinolates. These results demonstrate that (a) isothiocyanate levels in the crude plant extracts are extremely low; (b) myrosinase rapidly converts abundant glucosinolates to isothiocyanates; (c) hot water extraction releases over 70% of the inducer activity extractable with a triple solvent mixture permitting recovery of most of the biological activity in a preparation that is safe for human consumption; and (d) over 95% of the inducing potential in the intact plant is present as glucosinolates and therefore no other inducers are present in biologically significant quantities.

EXAMPLE 9

Development Regulation of Glucosinolate Production

Preliminary experiments in which field grown broccoli (cultivar DeCicco) was harvested at sequential time points from the same field indicated that on a fresh weight basis, inducer potential declined from the early vegetative stage through commercial harvest, but appeared to increase at late harvest (onset of flowering). These data suggested that inducer potential might be highest in seeds. Subsequent studies have shown that when seeds of 8 broccoli cultivars were surface sterilized and grown under gnotobiotic conditions, Phase 2 enzyme-inducer potential was highest in seeds and declined progressively (on a fresh weight basis) over time throughout the first 14 days of seedling growth.

Expressed on a per plant basis, however, activity remained constant over this period, suggesting that at this early stage of growth there was no net synthesis of glucosinolates. However, when the glucosinolate profiles of market stage broccoli heads and 3 day old sprouts (cultivar Emperor) were compared, there was a profound difference in the apparent glucosinolate compositions of these plants.

Sprouts were prepared by first surface sterilizing seeds of Brassica oleracea variety italica (broccoli) cultivar Emperor with a 1 minute treatment in 70% ethanol, followed by 15 min in 1.3% sodium hypochlorite with approximately 0.001% Alconox detergent. Seeds were grown in sterile plastic containers at a density of approximately 8 seeds/cm$^2$ for 72 hours on a 0.7% agar support that did not contain added nutrients. The environment was carefully controlled; broad spectrum fluorescent lighting, humidity and temperature control (16 hours light, 25° C./8 hours dark, 20° C.).

Plants were rapidly and gently collected from the surface of the agar to minimize glucosinolate hydrolysis by endogenous myrosinase released upon plant wounding. Sprouts [approximately 25 mg fresh wt/sprout], were gently harvested and immediately and rapidly plunged into approximately 3 volumes of boiling water in order to inactivate endogenous myrosinase as well as to extract glucosinolates and isothiocyanates from the plant tissue. Water was returned to a boil and maintained at a rolling boil for 3 min. The sprouts were then strained from the boiled infusion [tea, soup] and the infusion was stored at −20° C. until assayed.

Market stage heads were obtained by germinating seeds of the same seedlot in a greenhouse in potting soil, transplanting to an organically managed field in Garrett County, md and harvested at market stage. Heads were immediately frozen upon harvest, transported to the laboratory on ice and extracts were prepared in an identical fashion to those described above for sprouts except that approximately 3 gram floret tissue samples were used for extraction.

Inducer potential of plant extracts, prepared as described above, was determined by the microtiter plate bioassay method as described in Example 1. Paired ion chromatography revealed two major peaks, probably glucobrassicin and neo-glucobrassicin, in extracts of market stage heads with similar retention times to glucobrassicin (indole-3-ylmethyl glucosinolate) and neo-glucobrassicin (1-methoxyindole-3-ylmethyl glucosinolate). This observation is consistent with published reports on the glucosinolate composition of mature broccoli plants. However, paired ion chromatography under the same conditions of identically prepared extracts of 3-day-old sprouts showed absence of glucobrassicin or neo-glucobrassicin. Additionally, 3-day-old sprouts of different broccoli cultivars produce different mixtures of glucosinolates. Accordingly, glucosinolate production is developmentally regulated.

EXAMPLE 10

Evaluation of Anticarcinogenic Activities of Broccoli Sprout Preparations in the Huggins DMBA (9,10 Dimethyl-1,2-Benzanthracene) Mammary Tumor Model Sprouts were prepared by first surface sterilizing seeds of Brassica oleracea variety italica (broccoli) cultivar Saga with a 1 min treatment in 70% ethanol, followed by 15 min in 1.3% sodium hypochlorite with approximately 0.001% Alconox detergent. Seeds were grown in sterile plastic containers at a density of approximately 8 seeds/cm$^2$ for 72 hours on a 0.7% agar support that did not contain added nutrients. The environment was carefully controlled with broad spectrum fluorescent lighting, humidity and temperature control (16 hours light, 25° C./8 hours dark, 20° C).

The plants were rapidly and gently collected from the surface of the agar to minimize glucosinolate hydrolysis by endogenous myrosinase released upon plant wounding. A large quantity of sprouts was harvested by immediately and rapidly plunging into approximately 3 volumes of boiling water in order to inactivate endogenous myrosinase, as well as extracting glucosinolates and isothiocyanates from the plant tissue. Water was returned to a boil and maintained at a rolling boil for 3 min. Sprouts were then strained from the boiled infusion [tea, soup] and the infusion was lyophilized and stored as a dry powder at −20° C. [designated Prep A]. Other sprouts, similarly prepared were extracted with boiling water, cooled to 25° C. and were amended with a quantity of 7 day old daikon sprouts equivalent to approximately 0.5% of the original fresh weight of broccoli sprouts. This mixture was homogenized using a Brinkman Polytron Homogenizer and incubated at 37° C. for 2 hours following which it was filtered through a sintered glass filter, lyophilized as above and stored as a dried powder at −20° C. [designated Prep B].

QR inducer activity and inducer potential of plant extracts, prepared as described above, was determined by the microtiter plate bioassay method as described above. The induction of QR activity in preparation A is largely due to glucosinolates; predominantly glucoraphanin, which is the glucosinolate of sulforaphane, but this preparation also contains some glucoerucin, which is the sulfide analog of glucoraphanin. The induction QR activity of preparation B is almost exclusively due to isothiocyanates arising from treatment of glucosinolates with myrosinase.

Female Sprague-Dawley rats received at 35 days of age were randomized; 4 animals per plastic cage. All animals received 10 mg DMBA, by gavage in 1 ml sesame oil, at age 50 days. Sprout preparations (A or B) or vehicle control were given by gavage at 3, 2 & 1 day prior to DMBA, on the day of DMBA (2 hr prior to the DMBA dose) and on the day following DMBA dosing. The vehicle used was 50% Emulphor 620P/50% water. Animals were maintained on a semi-purified AIN-76A diet ad libitum from the time of receipt until termination of the experiment (167 days of age).

TABLE 4

ANTICARCINOGENIC ACTIVITIES OF BROCCOLI SPROUT EXTRACTS IN THE DMBA RAT MAMMARY TUMOR MODEL

| GROUP | TREATMENT | NUBMER OF ANIMALS AT TERMINATION | TOTAL TUMOR NUMBER | MULTIPLICITY: NUMBER OF TUMORS PER RAT |
|---|---|---|---|---|
| CONTROL | DMBA only | 19 | 34 | 1.79 |
| PREPARATION A (Glucosinolate) | 324 mg/dose (100 µmol sulforaphane equiv.) | 18 | 19 | 1.05 |
| PREPARATION B (Isothiocyanate) | 424 mg/dose (100 µmol sulforaphane equiv.) | 20 | 11 | 0.55 |

The development of palpable tumors was delayed for as much as 5 weeks by the administration of sprout extracts. Rats treated with either Preparation A or B had significantly fewer tumors than the untreated control, and the multiplicity of tumors (tumors per rat) was significantly lower in the animals receiving Preparations A or B.

EXAMPLE 11

Metabolism and Clearance of Glucosinolates in Humans

Two male, non-smoking volunteers ages 35 and 40 years, each in good health, were put on a low vegetable diet in which no green or yellow vegetables, or condiments, mustard, horseradish, tomatoes or papayas were consumed. After 24 hours on such a diet, all urine was collected in 8 hr aliquots. After 24 hours of baseline data, subjects ingested 100 ml of broccoli sprout soup (prepared as below), containing 520 µmol of glucosinolates.

The sprouts were prepared by first surface sterilizing seeds of Brassica oleracea variety italica (broccoli) cultivar Saga with a 1 min treatment in 70% ethanol, followed by 15 min in 1.3% sodium hypochlorite with ca. 0.001% Alconox detergent. Seeds were grown in sterile plastic containers at a density of approximately 8 seeds/cm$^2$ for 72 hours on a 0.7% agar support that did not contain added nutrients. The environment was carefully controlled with broad spectrum fluorescent lighting, humidity and temperature control (16 hours light, 25° C./8 hours dark, 20° C). The plants were rapidly and gently collected from the surface of the agar to minimize glucosinolate hydrolysis by endogenous myrosinase released upon plant wounding. A large quantity of sprouts was harvested by immediately and rapidly plunged into approximately 3 volumes of boiling water in order to inactivate endogenous myrosinase as well as to extract glucosinolates and isothiocyanates from the plant tissue. Water was returned to a boil and maintained at a rolling boil for 3 min. Following the boiling step, sprouts were homogenized directly in their infusion water for 1 min using a Brinkman Polytron Homogenizer and the preparations were frozen at −79° C. until use.

Inducer potential of plant extracts, prepared as described above, was determined by the microtiter plate bioassay method as described above. Inducer potential is nearly all due to glucosinolates; predominantly glucoraphanin, which is the glucosinolate of sulforaphane, but some glucoerucin which is the sulfide analog of glucoraphanin was also present. When converted to isothiocyanates by the addition of purified myrosinase, Phase 2 enzyme-inducing potential was 100,000 units/ml and contained 5.2 µmol of isothiocyanates per ml, as determined by the cyclocondensation reaction described in Example 7. Thus, the subjects consumed a total of 520 µmol of glucosinolates.

Collection of 8 hour urine samples was continued for an additional 30 hours. Urinary excretion of isothiocyanate conjugates (dithiocarbamates) was monitored using the cyclocondensation reaction as described in Example 7.

TABLE 5

EXCRETION OF DITHIOCARBAMATES BY TWO SUBJECTS INGESTING 520 MICROMOLES OF GLUCOSINOLATES EXTRACTED FROM SAGA BROCCOLI

| TIME Collection Time (hours) | CONDITION | SUBJECT 1 | SUBJECT 2 |
|---|---|---|---|
| | | µmol Dithiocarbamate per 8 hour urine collection | |
| 8 | baseline | 1.4 | 2.7 |
| 16 | baseline | 2.1 | 0.9 |
| 24 | baseline | 1.7 | 5.4 |
| 32 | 1st 8 hour post-dose | 23.2 | 20.4 |

TABLE 5-continued

EXCRETION OF DITHIOCARBAMATES BY TWO SUBJECTS
INGESTING 520 MICROMOLES OF GLUCOSINOLATES
EXTRACTED FROM SAGA BROCCOLI

| TIME Collection Time (hours) | CONDITION | SUBJECT 1 | SUBJECT 2 |
|---|---|---|---|
| | | μmol Dithiocarbamate per 8 hour urine collection | |
| 40 | 2nd 8 hour post-dose | 9.9 | 36.8 |
| 48 | 3rd 8 hour post-dose | 4.4 | 14.0 |
| 56 | 4th 8 hour post-dose | 4.2 | 4.1 |
| | Total post-dose minus average baseline: | 39.8 | 63.2 |
| | Total as Percent of dose: | 6.7% | 12.2% |

The two subjects studied metabolically converted a significant fraction of the ingested glucosinolates to the isothiocyanates which were converted to cognate dithiocarbamates and measured in the urine.

EXAMPLE 12

Effects of Physical Interventions on Sprout Growth on Production of Induces of Quinone Reductase Sprouts were prepared by first surface sterilizing seeds of *Raphanus sativum* (daikon) by a 1 minute treatment with 70% ethanol, followed by a 15 min treatment with 1.3% sodium hypochlorite with approximately 0.001% Alconox detergent. Seeds were grown in sterile plastic containers at a density of approximately 8 seeds/cm$^2$ for 7 days on a 0.7% agar support that did not contain added nutrients. The environment was carefully controlled with broad spectrum fluorescent lighting, humidity and temperature control (16 hours light 25° C./8 hours dark, 20° C.).

Treated sprouts were irradiated with germicidal UV light for 0.5 hr on days 5 and 6. Treated sprouts were only half the height of the untreated controls. Plants were harvested on day 7 by rapidly and gently collecting the plants from the surface of the agar to minimize glucosinolate hydrolysis by endogenous myrosinase released upon plant wounding. Sprouts were harvested by immediate and rapid plunging into approximately 10 volumes of DMF/ACN/DMSO (1:1:1) at approximately −50° C. in order to inactivate endogenous myrosinase as well as to extract glucosinolates and isothiocyanates. Sprouts were immediately homogenized with a ground glass mortar and pestle and stored at −20° C.

Inducer potential of plant extracts, prepared as described above, was determined by the microtiter plate bioassay method as described above. Inducer potential of the UV-treated sprouts was over three times that of untreated controls. Treatment of sprouts with ultraviolet light therefore increased the Phase 2 enzyme-inducer potential of the plant tissue.

Although the foregoing refers to particular preferred embodiments, it will be understood that the present invention is not so limited. It will occur to those of ordinary skill in the art that various modifications may be made to the disclosed embodiments and that such modifications are intended to be within the scope of the present invention, which is defined by the following claims. All publications and patent applications mentioned in this specification are indicative of the level of skill of those in the art to which the invention pertains.

All publications and patent applications are herein incorporated by reference to the same extent as if each individual publication or patent application were specifically and individually indicated to be incorporated by reference in its entirety.

What is claimed is:

1. A method of extracting glucosinolates and isothiocyanates from plant tissue comprising homogenizing said plant tissue in an excess of a mixture of dimethyl sulfoxide, acetonitrile and dimethylformamide at a temperature sufficient to inactivate myrosinase enzyme activity.

2. The method of claim 1, wherein the ratio of dimethyl sulfoxide:acetonitrile:dimethylformamide is 1:1:1.

3. The method of claim 1, wherein said temperature is between 0° C. and the freezing temperature of the extraction mixture.

4. The method of claim 1, wherein said temperature is between −50° C. and the freezing temperature of the extraction mixture.

5. The method of claim 1, wherein said plant tissue is selected from the group consisting of cruciferous sprouts measured after 3 days of growth, cruciferous seeds, plants or plant parts.

6. The method of claim 5, wherein said sprouts, seeds, plants or plant parts have at least 200,000 units per gram fresh weight of Phase 2 enzyme-inducing potential.

7. The method of claim 5, wherein said sprouts, seeds, plants or plant parts have at least 300,000 units per gram fresh weight of Phase 2 enzyme-inducing potential.

8. The method of claim 5, wherein said sprouts, seeds, plants or plant parts have at least 400,000 units per gram fresh weight of Phase 2 enzyme-inducing potential.

9. The method of claim 5, wherein said sprouts, seeds, plants or plant parts have at least 500,000 units per gram fresh weight of Phase 2 enzyme-inducing potential.

10. A method of making a food product comprising extracting glucosinolates and isothiocyanates from cruciferous plant tissue having at least 200,000 units per gram fresh weight of Phase 2 enzyme-inducing potential, recovering said glucosinolates and isothiocyanates and adding said glucosinolates and isothiocyanates to food;
wherein said extracting comprises contacting said plant tissue with a non-toxic solvent at a temperature sufficient to inactivate myrosinase enzyme activity.

11. The method according to claim 10, wherein said solvent is water.

12. The method of claim 11, wherein said water is at 100° C.

13. The method according to claim 10, wherein said solvent is liquid carbon dioxide.

14. The method according to claim 10, wherein said solvent is ethanol.

15. The method of claim 10, wherein said plant tissue is selected from the group consisting of cruciferous sprouts measured after 3 days of growth, cruciferous seeds, plants and plant parts.

16. The method of claim 15, wherein said sprouts, seeds, plants or plant parts have at least 300,000 units per gram fresh weight of Phase 2 enzyme-inducing potential.

17. The method of claim 15, wherein said sprouts, seeds, plants or plant parts have at least 400,000 units per gram fresh weight of Phase 2 enzyme-inducing potential.

18. The method of claim 15, wherein said sprouts, seeds, plants or plant parts have at least 500,000 units per gram fresh weight of Phase 2 enzyme-inducing potential.

19. The method of claim 10 wherein said food product is selected from the group consisting of a bread, a drink, a soup, a salad, a sandwich and a cereal.

20. The method of claim 19 wherein said drink is a tea.

21. The method of claim 10 wherein said extracting further comprises homogenizing said plant tissue with said non-toxic solvent.

22. The method of claim 15 wherein said sprouts, seeds, plants or plant parts have at least 250,000 units per gram fresh weight of Phase 2 enzyme-inducing potential.

23. The method of claim 15, wherein said plants are broccoli.

24. The method of claim 15, wherein said plant parts are from broccoli.

25. The method of claim 15, wherein said cruciferous sprouts are broccoli sprouts.

26. The method of claim 15, wherein said cruciferous seeds are broccoli seeds.

* * * * *